(12) United States Patent
Cho et al.

(10) Patent No.: US 8,993,787 B2
(45) Date of Patent: *Mar. 31, 2015

(54) METHOD FOR PREPARING 1,3,5-TRIOXANE

(75) Inventors: In Gi Cho, Gimcheon-si (KR); Jin Sang Choi, Gimcheon-si (KR); Kyung Min Kang, Gimcheon-si (KR)

(73) Assignee: KTP Industries, Inc., Gimcheon-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 13/882,266

(22) PCT Filed: Aug. 18, 2011

(86) PCT No.: PCT/KR2011/006063
§ 371 (c)(1),
(2), (4) Date: Jun. 19, 2013

(87) PCT Pub. No.: WO2012/057438
PCT Pub. Date: May 3, 2012

(65) Prior Publication Data
US 2013/0261319 A1    Oct. 3, 2013

(30) Foreign Application Priority Data
Oct. 29, 2010    (KR) .................. 10-2010-0107121

(51) Int. Cl.
C07D 323/06    (2006.01)
C07C 51/44    (2006.01)
A61K 9/00    (2006.01)
B01D 3/00    (2006.01)

(52) U.S. Cl.
CPC ............ C07D 323/06 (2013.01); A61K 9/0014 (2013.01); B01D 3/009 (2013.01)
USPC ............................................ 549/368; 203/14

(58) Field of Classification Search
CPC ................................ C07D 323/06; B01D 3/40
USPC ............................................ 549/368; 203/14
See application file for complete search history.

(56) References Cited

FOREIGN PATENT DOCUMENTS

| | | |
|---|---|---|
| JP | 06-228127 A | 8/1994 |
| KR | 10-2001-0097592 A | 11/2001 |
| KR | 10-2006-0043301 A | 5/2006 |

OTHER PUBLICATIONS

International Searching Authority, International Search Report of PCT/KR2011/006063 dated Apr. 30, 2012.

Primary Examiner — Andrew D Kosar
Assistant Examiner — Raymond Covington
(74) Attorney, Agent, or Firm — Sughrue Mion, PLLC

(57) ABSTRACT

The present invention relates to a method for preparing 1,3,5-trioxane using a distillation tower including a reactor, a distillation section, and an extraction section. Particularly, the present invention relates to a method for preparing 1,3,5-trioxane, in which the water phase separated from the stream discharged through the extraction unit of the reaction distillation tower is used in the process of extracting 1,3,5-trioxane.

3 Claims, 1 Drawing Sheet

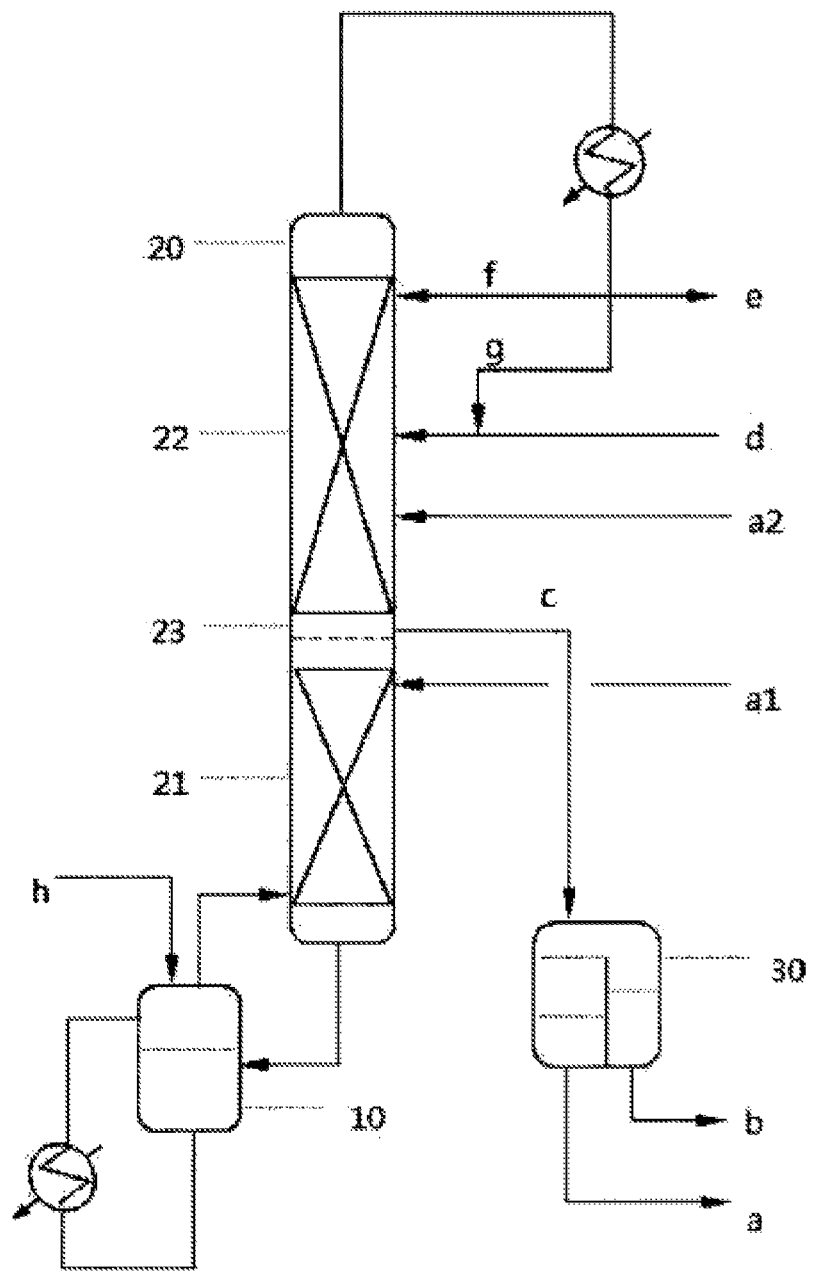

METHOD FOR PREPARING 1,3,5-TRIOXANE

TECHNICAL FIELD

The present invention relates to a method of preparing 1,3,5-trioxane using a reaction distillation tower including a reactor and a distillation tower provided with a distillation unit and an extraction unit.

BACKGROUND ART

Conventionally, 1,3,5-trioxane is obtained by the cyclization reaction of formaldehyde in the presence of an acid catalyst or a solid acid catalyst. A 1,3,5-trioxane-containing vapor obtained by the cyclization reaction is supplied from a reactor to a distillation tower. The 1,3,5-trioxane-containing vapor boiling in the distillation tower is concentrated and discharged, and then this concentrated 1,3,5-trioxane-containing vapor is extracted with a water-insoluble organic solvent. Further, the 1,3,5-trioxane-containing vapor boiling in the distillation tower may be directly extracted with a water-insoluble organic solvent. In both cases, 1,3,5-trioxane is extracted by both a distillation tower and an extraction tower, and an extracted liquid is converted into a solution containing a small amount of 1,3,5-trioxane by a fractionator, and then the solution is refluxed into the extraction tower.

For example, in the case of JP 1982-200383, a distillation tower and an extraction tower are separately provided in order to prepare 1,3,5-trioxane. 1,3,5-trioxane concentrated at the top of the distillation tower is introduced into the extraction tower, and is then extracted with a water-insoluble organic solvent. This method of preparing 1,3,5-trioxane disclosed in JP 1982-200383 is problematic in that equipment investment costs and operating costs excessively increase because a distillation tower and an extraction tower are separately provided in order to prepare 1,3,5-trioxane.

In order to overcome the above problems of increasing equipment investment costs and operating costs, there was proposed a distillation system in which a distillation unit and an extraction unit are integrally formed into one distillation apparatus and thus distillation and extraction processes are realized by the one distillation apparatus. However, this distillation system is also problematic in that, since a distillation unit and an extraction unit are integrally formed into one distillation apparatus, the concentration of formaldehyde in the extraction unit becomes high, so para-formaldehyde periodically accumulates in the extraction unit, with the result that a normal extraction process cannot be performed, and thus this distillation system must be frequently overhauled in order to perform a normal extraction process. Therefore, in order to prevent the accumulation of para-formaldehyde in this distillation system, there was an attempt to externally supply water into this distillation system. However, this attempt is also problematic in that the process is complicated and energy is excessively consumed because water must be discharged to the outside of the distillation system using a large amount of energy.

DISCLOSURE

Technical Problem

The present invention intends to provide a method of preparing 1,3,5-trioxane using a reaction distillation tower including a reactor and a distillation tower provided with a distillation unit and an extraction unit, which is characterized in that a water phase separated from a stream discharged from the extraction unit of the distillation tower is refluxed in a process of extracting 1,3,5-trioxane, so the concentration of formaldehyde in the extraction unit of the distillation tower is lowered, with the result that the precipitation of para-formaldehyde is prevented, and the total overhaul cycle in the process of preparing 1,3,5-trioxane is extended.

Technical Solution

An aspect of the present invention provides a method of preparing 1,3,5-trioxane using a reaction distillation tower including a reactor 10 and a distillation tower 20 provided with a distillation unit 21 and an extraction unit 22, wherein a water phase (a), which is separated from a stream discharged from the extraction unit 22 and then introduced into a decanter, is refluxed into the distillation unit 21 and the extraction unit 22.

In the method, the water phase (a) may be separated into a first water phase (a1) refluxed into the distillation unit 21 and a second water phase (a2) refluxed into the extraction unit 22.

In the method, the reflux ratio (f/e) of the water phase refluxed into the top of the distillation tower 20 to the water phase discharged to the outside of the distillation tower 20 may be 1.0 or more, and the reflux ratio (a2/f) of the second water phase (a2) refluxed into the extraction unit 22 to the water phase refluxed into the top of the distillation tower 20 may be 2.0 or more.

In the method, the concentration of formaldehyde in the extraction unit 22 of the distillation tower 20 may be 50 wt % or less.

DESCRIPTION OF DRAWINGS

FIG. 1 is a schematic view showing a reaction distillation tower used in the method of preparing 1,3,5-trioxane according to the present invention.

DESCRIPTION OF THE REFERENCE NUMERALS IN THE DRAWINGS

10: Reactor
20: Distillation tower
21: Distillation unit
22: Extraction unit
23: Side cut unit (Chimney-tray unit)
24: Extraction tower
30: Decanter

BEST MODE

Hereinafter, the present invention will be described in detail.

An embodiment of the present invention provides a method of preparing 1,3,5-trioxane using a reaction distillation tower including a reactor and a distillation tower provided with a distillation unit and an extraction unit, wherein a stream discharged from the extraction unit is introduced into a decanter to be separated into an oil phase and a water phase, and then the water phase is refluxed into the extraction unit, so the concentration of formaldehyde in the extraction unit of the distillation tower is lowered, with the result that the precipitation of para-formaldehyde can be prevented, and the total overhaul cycle in the process of preparing 1,3,5-trioxane can be extended.

Generally, a method of preparing 1,3,5-trioxane using a reaction distillation tower including a reactor and a distillation tower provided with a distillation unit and an extraction unit includes the processes of:

(1) producing a 1,3,5-trioxane-containing vapor from formaldehyde in the presence of an acid catalyst;

(2) distilling and extracting the 1,3,5-trioxane-containing vapor to separate 1,3,5-trioxane;

(3) separating the 1,3,5-trioxane-containing vapor into a water phase and an oil phase and then returning the water phase to the distillation tower; and (4) discharging water supplied to the reactor to the outside of a system.

The method of preparing 1,3,5-trioxane according to the present invention is characterized in that a stream is separated into an oil phase and a water phase in the process (3), the water phase is separated into a first water phase and a second water phase, and then the first water phase and the second water phase are respectively refluxed into the distillation unit and extraction unit of the distillation tower. That is, the second water phase is refluxed into the extraction unit of the distillation tower, so the concentration of formaldehyde in the extraction unit of the distillation unit is maintained in a predetermined concentration, with the result that the precipitation of para-formaldehyde can be prevented, and thus the total overhaul cycle in the process of preparing 1,3,5-trioxane can be extended.

Hereinafter, the present invention will be described in more detail with reference to the accompanying drawings.

In the reactor 10, 1,3,5-trioxane is prepared from formaldehyde in the presence of an acid catalyst. Formaldehyde, which is a raw material of 1,3,5-trioxane, is supplied into the reactor 10, and is then heated in the presence of an acid catalyst to synthesize 1,3,5-trioxane.

Formaldehyde, which is a raw material used to synthesize 1,3,5-trioxane, may exist in the form of formaldehyde gas, an aqueous formaldehyde solution, para-formaldehyde or the like. Preferably, an aqueous formaldehyde solution may be used in terms of tractability.

The acid catalyst may be a homogeneous catalyst. A solid acid catalyst may be used as the acid catalyst. Examples of the acid catalysts may include mineral acids, such as sulfuric acid, phosphoric acid and the like; strong organic acids, such as sulfonic acid, phosphonic acid, trifluoroacetic acid and the like; solid acids, such as a strong-acid cation exchanger, zeolite, silica, alumina, active white clay and the like; and heteropoly acids, such as phosphomolybdic acid, phosphotungstenic acid and the like.

1,3,5-trioxane synthesized in the reactor 10 is supplied to the distillation tower 20. Specifically, a 1,3,5-trioxane-containing vapor is supplied to the distillation tower 20. The 1,3,5-trioxane-containing vapor includes 1,3,5-trioxane, formaldehyde, water and other side-reactants.

In the distillation tower 20, the 1,3,5-trioxane-containing vapor supplied from the reactor 10 is distilled and extracted to separate 1,3,5-trioxane. The distillation tower 20 includes a distillation unit 21 and an extraction unit 22. If the distillation tower 20 is divided into upper and lower portions, the distillation unit 21 is located at the lower portion of the distillation tower 20, and the extraction unit 22 is located at the upper portion thereof. The distillation tower 20 may be provided with a side cut unit 23 such as a chimney tray between the distillation unit 21 and the extraction unit 22. The 1,3,5-trioxane-containing vapor supplied from the reactor 10 is introduced into the distillation unit 21, is distilled, and is then introduced into the extraction unit. Further, the water phase (a) returning to the distillation unit 21 from the following decanter 30 condenses the 1,3,5-trioxane-containing vapor rising up to the distillation unit 21. The formaldehyde included in the condensed 1,3,5-trioxane-containing vapor can be reused in the reactor 10 for synthesizing 1,3,5-trioxane.

In the extraction unit 22, an extractant is supplied to the extraction unit 22 through a stream (d) in order to separate 1,3,5-trioxane from the 1,3,5-trioxane-containing vapor supplied from the distillation unit 21, and a part of the extractant is azeotropically boiled with water in the extraction unit 22 to flow upwards. In this case, in the extraction unit 22, the 1,3,5-trioxane-containing vapor interacts with the extractant to cause a partial condensation phenomenon, thus increasing the concentration of formaldehyde in the liquid of the extraction unit 22. Further, in this azeotripic distillation procedure, the extractant may be discharged from the top of the distillation tower 20 together with the 1,3,5-trioxane-containing vapor. The extractant in the vapor is refluxed into the extraction unit 22 through a stream (g), and a part of a water phase in the vapor is discharged to the outside of the distillation tower 20 through a stream (e), and a residue of the water phase in the vapor is refluxed into the extraction unit 22 through a stream (f). Here, in order to maintain the concentration of formaldehyde in the extraction unit 22, the reflux ratio (f/e) of the water phase refluxed into the top of the distillation tower 20 to the water phase discharged to the outside of the distillation tower 20 may be 1.0 or more.

In the extraction unit 22, an extractant is externally supplied into the extraction unit through the stream (d) in order to separate 1,3,5-trioxane. The extractant for separating 1,3,5-trioxane may be an organic solvent that can be azeotropically boiled with water. Specific examples of the organic solvent may include halogenated aliphatic hydrocarbons such as methylene chloride, chloroform, carbon tetrachloride, ethylene chloride and the like; halogenated aromatic hydrocarbons such as chlorobenzene, o-chlorobenzene and the like; and aromatic hydrocarbons such as benzene, toluene and the like. Among these organic solvents, benzene can be preferably used.

Meanwhile, the 1,3,5-trioxane-containing liquid phase separated from the extraction unit 22 is supplied to a decanter 30 through a stream (c) discharged from a side cut unit 23. In this case, the stream (c) discharged from the side cut unit 23 may include 1,2,5-trioxane, formaldehyde, an extractant, water and other side-products. The stream (c) supplied to the decanter 30, as described later, is separated into a water phase (a) and an oil phase (b), and the water phase (a) is separated into a first water phase (a1) and a second water phase (a2), and the second water phase (a2) is refluxed into the extraction unit 22.

If the second water phase (a2) is refluxed from the decanter 30 into the extraction unit 22, the second water phase (a2) may be refluxed between the extractant supply stream (d) and the 1,3,5-trioxane discharge stream (c). When a suitable amount of the second water phase (a2) is refluxed into the extraction unit 22, the concentration of formaldehyde in the extraction unit 22 between the extractant supply stream (d) and the 1,3,5-trioxane discharge stream (c) can be maintained at 50 wt % or less. In contrast, when the concentration of formaldehyde is excessively high, a possibility of precipitating formaldehyde increases, thus causing a difficulty in operating the distillation tower 20.

In conclusion, when the second water phase (a2) is refluxed into the extraction unit 22 of the distillation tower 20, the concentration of formaldehyde in the extraction unit 22 can be maintained to such a degree that para-fromaldehyde is not precipitated, so it is possible to extend the overhaul cycle in the overall process including the distillation tower 20. Further, when the second water phase (a2) is refluxed into the extraction unit 22 of the distillation tower 20, there is an advantage in that it is possible to prevent the problem that water must be discharged to the outside of a system using a large amount of energy when water is externally supplied in order to lower the concentration of formaldehyde. In this case, in order to suitably maintain the concentration of formaldehyde in the extraction unit 22, the reflux ratio (a2/f) of the second water phase (a2) refluxed into the extraction unit 22 to the water phase refluxed into the top of the distillation tower 20 may be 2.0 or more.

In the decanter 30, the stream (c) discharged from the side cut unit 23 of the distillation tower 20 is phase-separated. The stream (c) introduced into the decanter 30, as described above, is a liquid phase, and includes 1,2,5-trioxane, formaldehyde, an extractant, water and other side-products. The stream (c) introduced into the decanter 30 is separated into a water phase (a) and an oil phase (b), and the water phase (a) is separated into a first water phase (a1) and a second water phase (a2), and the first water phase (a1) is refluxed into the distillation unit 21 and the second water phase (a2) is refluxed into the extraction unit 22. In this case, the oil phase (b) may include 1,3,5-troxane, an extractant and other side products, and the first water phase (a1) and second water phase (a2) may include 1,3,5-troxane, formaldehyde, water and other side products. The side products included in the first water phase (a1) and second water phase (a2) may include methanol, formic acid, methylal, oxymethylenedimethoxide, methyl formate, and the like.

MODE FOR INVENTION

Hereinafter, the present invention will be described in more detail with reference to the following Examples. However, the scope of the present invention is not limited to these Examples.

EXAMPLE 1

1,3,5-trioxane was prepared using a reaction distillation tower shown in FIG. 1. The reaction distillation tower includes a distillation tower 20 provided with a distillation unit 21 (diameter 30 mm, 15 stages, bubble-cap tray), an extraction unit 22 (diameter 50 mm, 20 stages, bubble-cap tray) and a side cut unit 23 (one stage, chimney tray) disposed between the distillation unit 21 and the extraction unit 22, a reactor 10 (volume 5 L, provided with a heating unit) and a decanter (volume 1.5 L).

An aqueous solution containing formaldehyde in a concentration of 65.0 wt % was supplied to the reactor 10 at a flow rate of 400 g/hr, and the concentration of sulfuric acid in a reaction solution was set to 2.0 wt %. A 1,3,5-trioxane-containing vapor produced by steam heating of 1400 g/hr was supplied to the distillation unit 21 of the distillation tower 20.

The 1,3,5-trioxane-containing vapor was supplied to the extraction unit 22, and simultaneously benzene was supplied to the extraction unit 22 as an extractant through a to stream (d).

The 1,3,5-trioxane-containing vapor supplied to the distillation unit 21 was introduced into the extraction unit 22, was discharged from the side cut unit 23 through a stream (c) together with benzene supplied to the extraction unit 22, and was then phase-separated into a water phase (a) and an oil phase (b). Then, the oil phase (b) was balanced with benzene supplied to the extraction unit 22 by adjusting the flow rate of the oil phase (b) to 620 g/hr.

The water phase (a) was separated into a first water phase (a1) and a second water phase (a2) in the decanter 30. The second water phase (a2) was supplied between a benzene supply stream (d) and the side cut unit 23, and the first phase (a1) was refluxed into the distillation unit 21 in order to maintain the interface of the water phase (a) in the decanter 30.

A part of benzene supplied through the extractant supply stream (d) was azeotropically boiled with water by the steam supplied to the reactor 10, and was then discharged from the top of the distillation tower 20. The discharged benzene was reused through a stream (g). A part of water supplied to the reactor 10 was discharged through a stream (e), and residual water was refluxed to the top of the distillation tower 20 through a stream (f).

For this purpose, in the stream (e), the flow rate of water was maintained at 162 g/hr, and, in the stream (f), the flow rate thereof was maintained at 300 g/hr. In this case, the composition obtained from the top of the distillation tower 20 includes 84.0 wt % of water, 11.6 wt % of formaldehyde and 4.4 wt % of a residue.

The results obtained after 20 hours from the operation start point are given in Table 1 below. The concentration of formaldehyde in the distillation tower 20 between the benzene supply stream (d) and the side cut unit 23 was 44.5 wt %.

COMPARATIVE EXAMPLE 1

1,3,5-trioxane was prepared using the same reactor 10, distillation tower 20 and decanter 30 as in Example 1 in the same manner as in Example 1, except that the water phase (a) discharged from the decanter 30 was directly refluxed into the distillation unit 21 without being separated into a first water phase (a1) and a second water phase (a2).

The results obtained after 20 hours from the operation start point are given in Table 1 below. The concentration of formaldehyde in the distillation tower 20 between the benzene supply stream (d) and the side cut unit 23 was 57.0 wt %.

COMPARATIVE EXAMPLE 2

1,3,5-trioxane was prepared using the same reactor 10, distillation tower 20 and decanter 30 as in Example 1 in the same manner as in Example 1, except that the water phase (a) discharged from the decanter 30 was directly refluxed into the distillation unit 21 without being separated into a first water phase (a1) and a second water phase (a2), and this water phase (a) was heated by the steam supplied to the reactor 10 at a flow rate of 1000 g/hr, so the flow rate of the water phase (a) in the stream (e) was maintained at 175 g/hr, and the flow rate thereof in the stream (f) was maintained at 156 g/hr.

The results obtained after 20 hours from the operation start point are given in Table 1 below. The concentration of formaldehyde in the distillation tower 20 between the benzene supply stream (d) and the side cut unit 23 was 61.0 wt %.

COMPARATIVE EXAMPLE 3

1,3,5-trioxane was prepared using the same reactor 10, distillation tower 20 and decanter 30 as in Example 1 in the same manner as in Example 1, except that the water phase (a) discharged from the decanter 30 was separated into a first water phase (a1) and a second water phase (a2), and the second water phase (a2) was supplied between the benzene supply stream (d) and the side cut unit 23 at a flow rate 310 g/hr.

The results obtained after 20 hours from the operation start point are given in Table 1 below. The concentration of formaldehyde in the distillation tower 20 between the benzene supply stream (d) and the side cut unit 23 was 51.0 wt %.

In each of the 1,3,5-trioxane preparation processes of Example 1 and Comparative Examples 1 to 3, the concentration of formaldehyde in the extraction unit 22 was analyzed using the following method.

The concentration of formaldehyde in the extraction unit 22 was analyzed using gas chromatography (detector TCD, separation tube APS-201 20% Flusin T 30-60 mesh 4m). 1 μL of a sample was taken by a 10 μL syringe, and was then analyzed by gas chromatography under conditions of an inlet temperature of 170° C., a detector temperature of 150° C., a separation tube temperature of 110° C. and a helium gas flow rate of 20 mL/min.

TABLE 1

|  |  | Unit | Ex. 1 | Comp. Ex. 1 | Comp. Ex. 2 | Comp. Ex. 3 |
|---|---|---|---|---|---|---|
| Concentration of formaldehyde in extraction unit | "f" stream | wt % | 11.6 | 12.0 | 19.5 | 11.8 |
|  | "d~a2" stream | wt % | 43.0 | 51.0 | 56.0 | 48.5 |
|  | "a2~c" stream | wt % | 44.5 | 57.0 | 61.0 | 51.0 |
|  | "c" stream | wt % | 36.5 | 36.7 | 36.5 | 36.7 |
| Reflux ratio into distillation tower | "f/e" ratio | — | 1.86 | 1.86 | 0.89 | 1.86 |
|  | "a2/f" ratio | — | 3.43 | — | — | 1.04 |
| Supply stream into reactor | steam | g/hr | 1400 | 1400 | 1000 | 1400 |
|  | formaldehyde (65 w %) | g/hr | 400 | 400 | 400 | 400 |

From the results of measuring the concentration of formaldehyde in the extraction unit 22 in each of the 1,3,5-trioxane preparation processes of Example 1 and Comparative Examples 1 and 2, as given in Table 1 above, it can be ascertained that the concentration of formaldehyde in the extraction unit 22 increases when the water phase (a) discharged from the decanter 30 is directly refluxed into the distillation unit 21 without being separated into a first water phase (a1) and a second water phase (a2) (Comparative Examples 1 and 2), or when the amount of the second water phase (a2) to refluxed into the extraction unit 22 is small, even though the water phase (a) is separated into the first water phase (a1) and the second water phase (a2) (Comparative Example 3).

Therefore, it can be ascertained that, in the process of preparing 1,3,5-trioxane using the reaction distillation tower shown in FIG. 1, when the water phase (a) discharged from the decanter 30 was separated into a first water phase (a1) and a second water phase (a2) and then the first water phase (a1) and the second water phase (a2) were respectively refluxed into the distillation unit 21 and the extraction unit 22, the concentration of formaldehyde in the extraction unit can be maintained at 50 wt % or less.

The invention claimed is:

1. A method of preparing 1,3,5-trioxane using a distillation apparatus comprising a reactor 10, a distillation tower 20, and a decanter 30, wherein the distillation tower 20 comprises a distillation unit 21 and an extraction unit 22 within the tower, said method comprising
    preparing 1,3,5-trioxane-containing vapor from formaldehyde in the reactor 10;
    distilling the 1,3,5-trioxane-containing vapor in the distillation unit 21;
    introducing the distilled 1,3,5-trioxane-containing vapor into the extraction unit 22 and subjecting the distilled 1,3,5-trioxane-containing vapor to an extraction with an organic solvent to produce a vapor phase and a liquid phase, said organic solvent being capable of being azeotropically boiled with water;
    wherein the liquid phase is introduced into the decanter 30 where the liquid phase is separated into a water phase (a) and an oil phase (b); and
    wherein the water phase (a) is separated into a first water phase (a1) refluxed into the distillation unit 21 and a second water phase (a2) refluxed into the extraction unit 22.

2. The method of preparing 1,3,5-trioxane according to claim 1, wherein the vapor phase in the extraction unit 22 contains water and a part of the water (f) is refluxed into the top of the distillation tower 20 and the remaining of the water (e) is discharged to the outside of the distillation tower 20, and wherein a ratio (f)/(e) is 1.0 or more; and
    wherein ratio of the second water phase (a2) refluxed into the extraction unit 22 to the water (f) refluxed into the top of the distillation tower 20 is 2.0 or more.

3. The method of preparing 1,3,5-trioxane according to claim 1, wherein the vapor phase and the liquid phase in the extraction unit 22 contain formaldehyde and the concentration of the formaldehyde in the extraction unit 22 is 50 wt % or less of the total weight of the vapor phase and the liquid phase in the extraction unit 22.

\* \* \* \* \*